(12) United States Patent
Duval

(10) Patent No.: US 8,664,185 B2
(45) Date of Patent: Mar. 4, 2014

(54) METHOD FOR PREPARING POLYPHENOL EXTRACTS FROM SPINACH LEAVES

(75) Inventor: Charles Duval, Macon (FR)

(73) Assignee: Naturex, Montfavet, Avignon (FR)

( * ) Notice: Subject to any disclaimer, the term of this patent is extended or adjusted under 35 U.S.C. 154(b) by 0 days.

(21) Appl. No.: 13/318,887

(22) PCT Filed: May 4, 2010

(86) PCT No.: PCT/FR2010/050848
§ 371 (c)(1),
(2), (4) Date: Apr. 18, 2012

(87) PCT Pub. No.: WO2010/128243
PCT Pub. Date: Nov. 11, 2010

(65) Prior Publication Data
US 2012/0196818 A1 Aug. 2, 2012

(30) Foreign Application Priority Data

May 4, 2009 (FR) ..................................... 09 52947

(51) Int. Cl.
*A61K 31/7048* (2006.01)
(52) U.S. Cl.
USPC .......................................................... 514/27
(58) Field of Classification Search
USPC .......................................................... 514/27
See application file for complete search history.

(56) References Cited

U.S. PATENT DOCUMENTS

2006/0201056 A1* 9/2006 Jordan ............................ 44/307
2008/0138393 A1 6/2008 Leverett et al.

OTHER PUBLICATIONS

Edenharder et al. Isolation and Characterization of Structurally Novel Antimutagenic Flavonoids from Spinach (*Spinacia oleracea*). J Agr Food Chem 49:2767-2773, 2001.*
Berquist, et al., "Flavonoids in baby spinach (*Spinacia oleraceaL*.): Changes during plant growth and storage", Journal of Agricultural and Food Chemistry, vol. 53, No. 24, Nov. 2005, pp. 9459-9464.
Ferreres, et al., "Acylated flavonol glycosides from spinach leaves (*Spinacia oleracea*)", Phytochemistry, Pergamon Press, GB, vol. 45, No. 8, Aug. 1, 1997, pp. 1701-1705.
Lomnitski, et al., "Composition, Efficacy, and Safety of Spinach Extracts", Nutrition and Cancer, London, GB, vol. 46, No. 2, Jan. 1, 2003, pp. 222-231.
International Search Report issued on Oct. 7, 2010 for International Application No. PCT/FR2010/050848.

* cited by examiner

*Primary Examiner* — Wu-Cheng Winston Shen
*Assistant Examiner* — Yih-Horng Shiao
(74) *Attorney, Agent, or Firm* — Knobbe, Martens, Olson & Bear, LLP

(57) ABSTRACT

A method for preparing a concentrated spinach extract in a liquid or dry form and having a polyphenol titer greater than or equal to 50% is described. The method includes a step of purifying a raw spinach extract in a liquid form using a liquid-liquid extraction technique with a food oil.

7 Claims, 1 Drawing Sheet

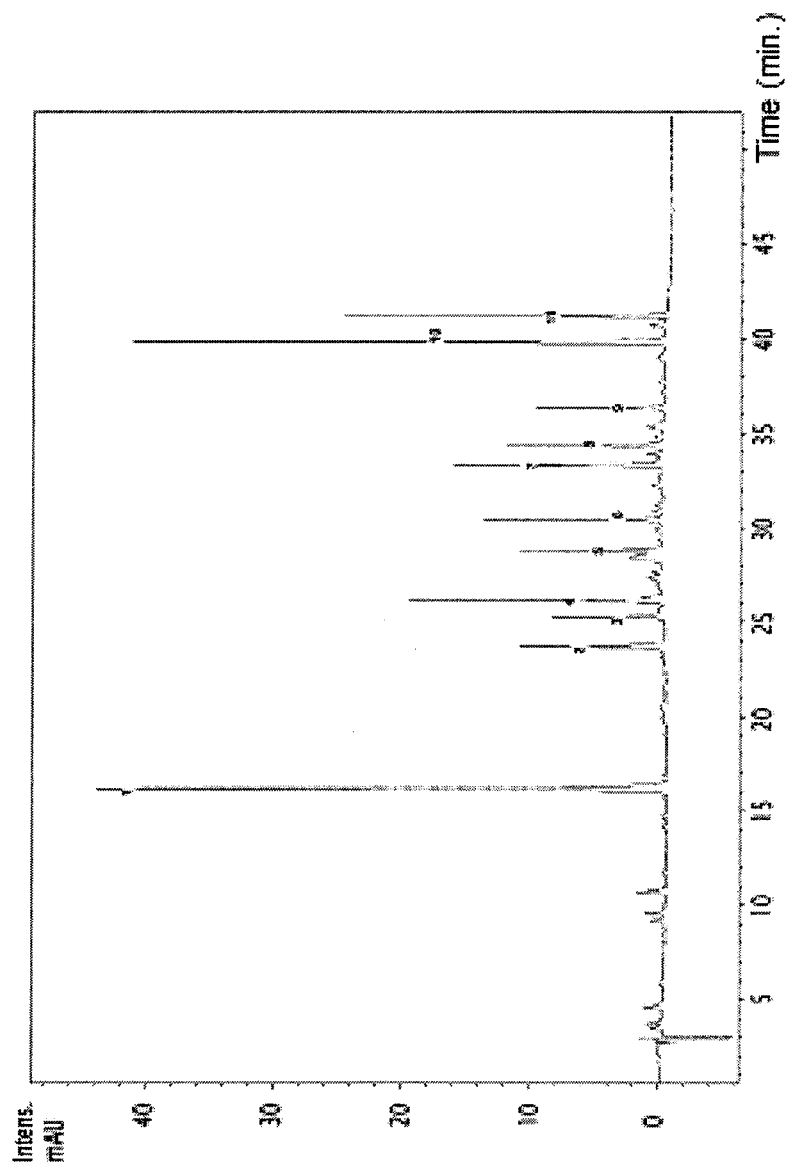

METHOD FOR PREPARING POLYPHENOL EXTRACTS FROM SPINACH LEAVES

CROSS-REFERENCE TO RELATED APPLICATIONS

This application is the U.S. National Phase under 35 U.S.C. §371 of International Application PCT/FR2010/050848, filed May 4, 2010, which was published in a non-English language, which claims priority to FR 0952847, filed May 4, 2009.

BACKGROUND OF THE INVENTION

1. Field of the Invention

The subject of the present invention is a novel method for preparing concentrated, purified polyphenol extracts from spinach leaves.

2. Description of the Related Art

Spinach (*Spinacia oleracea*) is an annual or biennial vegetable plant of the Chenopodiaceae family. This plant is commonly cultivated and eaten as part of a normal diet.

In traditional use, spinach is considered inter alia to be fortifying, revitalizing, muscle toning, toning the heart muscles in particular. It is high in carotenes, vitamins (particular C, E), mineral and trace elements (particularly magnesium, iron, calcium, potassium) meaning that it is an excellent indication against general fatigue and depressive states.

Spinach is also traditionally used for its anti-anaemic properties.

Spinach leaves contain polyphenols of flavonol type, and flavonols in simple or polymerized form.

These polyphenols are known to be good antioxidants and anti-inflammatories.

SUMMARY OF THE INVENTION

It is therefore an objective of the present invention to provide a method for preparing concentrated spinach extracts high in polyphenols.

A further objective of the present invention is to provide spinach extracts having high polyphenol content, the said extracts therefore being intended for applications to improve the performance levels of the striated muscles in man or animal.

The present invention concerns a method for preparing a concentrated spinach extract in liquid or dry form, having a polyphenol titre equal to or more than 50%, comprising a step to purify a raw spinach extract in liquid form using a liquid-liquid extraction technique with a food oil.

According to one preferred embodiment, the food oil is chosen from the group composed of olive oil, sunflower oil, grape-seed oil, fish oil and mixtures thereof.

Therefore, the method according to the present invention comprises the following steps:
- food oil is added to the raw extract in liquid form, to obtain a raw liquid extract with added food oil,
- the said raw liquid extract with added food oil is subjected to a vacuum concentration step under agitation, to obtain a supernatant oil phase comprising the chlorophyll and carotenoid pigments and an aqueous phase comprising the water-soluble compounds (carbohydrates, proteins, simple or complex phenol compounds . . . ), and
- the oil phase and water phase are isolated separately.

The extraction step of the raw liquid extract according to the invention with food oil allows a refined extract to be obtained having a high content of active ingredient(s). For this purpose, the said raw extract is subjected to a purification step. This purification step is conducted by combining two steps. The objective of the first step is to remove the colouring compounds of chlorophyll type whilst obtaining a recoverable product as green food colouring of high quality, the pigments having been protected against phenomena of degradation by oxidation which generally occur in the course of concentration by these means.

The addition is made to the raw extract in liquid form of ordinary food oil, of olive, sunflower, grape-seed, fish oil type or any other food oil of identical characteristics in proportions ranging from 1:1 to 1:1000 in relation to the desired chlorophyll concentration. The raw liquid extract with added oil is then concentrated in vacuo under agitation using equipment of evaporator-concentrator type or a ball vacuum concentrator. This step also allows a reduction in the volume of the product and the removal of alcohol if extraction uses a hydro-alcoholic mixture. The product obtained is in the form of a two-phase mixture, the supernatant oil phase containing the chlorophyll and carotenoid pigments protected against oxidative phenomena, the aqueous phase comprising all the water-soluble compounds such as carbohydrates, proteins and simple or complex phenol compounds. The separation of the mixture can be improved by adding a sufficient proportion of water.

In the method of the present invention, the above-mentioned oil phase is then recovered and is preferably subjected to one or more washing steps with water, and optionally dried to obtain a powder colouring agent.

The above-mentioned washing step of the oil phase with water allows an increase in the recovered water-soluble compounds which may have emulsified with the oil phase.

This oil phase can be directly re-used as natural, even biological, green food colouring, starting from spinach derived from organic farming. This oil phase can also be dried by spray drying, using suitable drying media such as caseinates, maltodextrins, lecithins, to obtain a water-dispersible colouring powder.

The collected aqueous phase such as defined above, notably containing polyphenols, can be dried directly or it can undergo a second refining.

Therefore, according to one particular embodiment of the method of the invention, the aqueous phase obtained after the extraction step with food oil is collected and dried to obtain a concentrated extract in dry form.

According to another particular embodiment of the invention, the aqueous phase obtained after the extraction step with food oil is collected then subjected to a purification step to obtain a purified concentrated extract.

This complementary purification step can be carried out by passing through adsorbent resins and eluting with a solvent of alcohol type, or by liquid-liquid extraction using a solvent non-miscible in water such as ethyl acetate, butanol or any other solvent having affinity with the phenol compounds.

The chromatography resins used may be of ion exchange type for example (anions or cations), or of adsorption/desorption type for example of divinylbenzene/styrene copolymer, polystyrene or polymethacrylic type marketed in particular by Rohm & Haas or Mitsubishi Chemical.

The method of the invention may comprise additional steps consisting of obtaining extracts having a higher concentration of active ingredients.

For example, the purified extract obtained after the purification step using chromatography or liquid-liquid extraction with ethyl acetate or butanol, can then be concentrated either by in vacuo evaporation or by membrane nano-filtration, in order to obtain a concentrate containing between 15 and 70% of dry matter.

Finally, this purified concentrate can then be dried using equipment such as a spray dryer, freeze-dryer or vacuum drier.

The present invention therefore also concerns the preparation of a purified concentrated extract in dry form, the said dry form being obtained by drying a purified concentrated extract in liquid form.

According to one preferred embodiment, the drying steps conducted to obtain dry forms are carried out by spray drying.

The present invention also concerns a method such as defined above, characterized in that the raw spinach extract in liquid form is obtained using a method comprising an extraction step which places the spinach in fresh or frozen form in the presence of a solvent chosen from the group comprising water, ethanol and mixtures thereof.

According to one preferred embodiment, the spinach used in the method of the invention originates from the whole plant, in fresh or dry form.

The raw spinach extract according to the invention is obtained by placing the plant, in its fresh or frozen form, in the presence of a solvent such as water, ethanol or a mixture of water and ethanol in proportions possibly ranging from 100:0 to 0:100, for an extraction step, separating the plant and the solvent in order to obtain a raw extract in liquid form. To obtain a raw extract in dry form, the raw extract in liquid form is dried for example by removing water in a hot air stream, by atomization, by evaporation, by sublimation, by dehydration, by adsorption on a substrate.

The present invention also concerns a method for preparing a colouring product, comprising the following steps:
   food oil is added to a raw spinach extract such as defined above in liquid form, to obtain a raw liquid extract with added food oil,
   the said raw liquid extract with added food oil is subjected to a concentration step in vacuo and under agitation, to obtain a supernatant oil phase comprising the chlorophyll and carotenoid pigments and an aqueous phase comprising the water-soluble compounds,
   the oil phase is collected and subjected to one or more washing steps with water to obtain a liquid colouring product, and optionally the washed oil phase is dried to obtain a colouring powder.

This method therefore allows a colouring product to be obtained in liquid form or dry form.

The present invention therefore also concerns a colouring product, in liquid or dry form, which can be obtained using the method such as defined above.

The said colouring product in liquid form can also be used as green food colouring.

The present invention also concerns a concentrated spinach extract, which can be obtained following the above-defined preparation method.

The concentrated extracts of the invention are characterized in that they have a titre of total polyphenols that is equal to or higher than 50%.

The present invention also concerns a concentrated spinach extract, in liquid or dry form, with a titre of total polyphenols equal to or higher than 50%, preferably between 60% and 100%, more preferably between 90% and 100%.

The polyphenols are assayed by spectrophotometry and HPLC (for example according to the method described below).

Preferably, the extracts of the invention mostly comprise polyphenol compounds and preferably to the proportion of at least 70% by weight (relative to the total weight of the extract).

Amongst these polyphenol compounds, those essentially found are of the flavonoid family and in particular the chemical class of flavonols.

Therefore, the four major polyphenol representatives which enter into the composition of the spinach extracts of the invention are the following: patuletin, spinacetin, jaceidin and spinatoside (in simple or glucosylated form).

More exactly, the spinach extracts of the invention comprise the following compounds:
patuletin-3-glucosyl-(1-6)-apiosyl(1-2)-glucoside,
patuletin-3-glucosyl-(1-6)-glucoside,
spinacetin-3-glucosyl-(1-6)-apiosyl(1-2)-glucoside,
spinacetin-3-glucosyl-(1-6)-glucoside,
spinacetin-3-feruloylglucosyl-(1-6)-glucoside,
spinatoside,
jaceidin-4'-glucuronide,
5,3',4'-trihydroxy-3-methoxy-6:7-methylenedioxyflavone-4'-glucuronide,
5,4'-dihydroxy-3,3'-dimethoxy-6:7-methylenedioxyflavone-4'-g lucuronide.

Phenolic acids are also present in the extracts of the invention, in particular o-coumaric acid, ferulic acid, p-coumaric acid and glucuronic acid.

Ecdysteroids commonly called phytoecdysteroids (in majority 20-hydroxyecdyone) are also present in the extracts of the invention.

The present invention also concerns a pharmaceutical composition comprising a spinach extract such as defined above, in combination with a pharmaceutically acceptable vehicle.

The present invention also concerns a food supplement comprising a spinach extract such as defined above, in combination with an acceptable vehicle.

The spinach extracts of the invention are intended for various applications, in particular for the improvement of the performance levels of the striated muscles in man or animal. Therefore the consumption of the said extract allows the reducing of compounds derived from muscle oxidative metabolism and derivative metabolites which deteriorate muscle performance and increase recovery time.

The present invention also concerns the use of the said extract in preparations in different galenic forms, for administration to man or animal, whether in the form of a medication or food supplement, or health product.

The application of the said preparations concerns all human or animal populations, in which the contribution towards improved muscle performance and an increase in recovery capacity is of interest, as in experienced sports persons, those occasionally practising a sport requiring assistance for recovery after effort, elderly persons having difficulty in recovering after a physical activity and racing animals or animals of old age.

According to one preferred embodiment, the present invention concerns the spinach extracts such as defined above for use thereof to improve muscle performance.

The present invention also concerns the spinach extracts such as defined above for use thereof in the treatment and prevention of musculoskeletal disorders.

The present invention also concerns the spinach extracts such as defined above for use thereof in the treatment and prevention of muscular disorders following after effort.

BRIEF DESCRIPTION OF THE DRAWINGS

FIG. 1 illustrates the UV chromatogram at 280 nm of a purified spinach extract obtained using the method of the invention (purified extract No. 1—cf. examples).

DETAILED DESCRIPTION OF THE INVENTION

Assay Method Of The Polyphenols

The method conducted for the assay of total polyphenols is the following.

The chromatographic system used is the Agilent Technologies system, 1100 series.

The different polyphenols are separated using a Kromasil C18 column, 250 mm×4.6 mm—5 µm, equipped with a pre-column of the same type.

Reagents

As solvents: Ultra-Pure Millipore water, acetonitrile (Chimie Plus, ref: AC03902500), methanol (Chimie Plus, ref: ME03102500), 85% orthophosphoric acid (Fisher Scientific, ref: O/0450/PB15) and glacial acetic acid (Fisher Scientific, ref: A/0400/PB15).

As analytical standards: gallic acid (Extrasynthese, ref: 4993 S), catechin (Extrasynthese, ref: 0976 S), epicatechin (Extrasynthèse, ref: 0977 S), epicatechin gallate (Extrasynthèse, ref: 0978 S), procyanidin B1 (Extrasynthèse, ref: 0983) and procyanidin B2 (Extrasynthèse, ref: 0984).

Operating Mode

1. Chromatographic Conditions:

The elution solvents are the following:
solvent A: HPLC quality water acidified to pH 2.5 with orthophosphoric acid;
solvent B: acetonitrile/acetic acid 90:10

The flow rate of the mobile phase is 1 mL/min.

The temperature of the column is 25° C.

The injection volume is 20 µL and detection is performed in UV at 280 nm for an analysis time of 50 minutes.

The following gradient is applied:

| Time (min) | % solvent A | % solvent B |
|---|---|---|
| 0 | 95 | 5 |
| 30 | 75 | 25 |
| 35 | 70 | 30 |
| 45 | 50 | 50 |
| 50 | 40 | 60 |

2. Solutions to be Prepared

Solubilisation Solvent:
ultrapure water/methanol, HPLC quality/glacial acetic acid
75:20:5 (v/v/v)

Standard Solution

In a 10 mL volumetric flask are weighed 5 mg of gallic acid, 5 mg of catechin, 5 mg of epicatechin, 5 mg of epicatechin gallate, 2 mg of procyanidin B1 and 2 mg of procyanidin B2.

These are all dissolved and the solution completed to volume with methanol.

Sample Solution to be Analyzed 100 mg of extract to be analyzed are weighed in a 50 mL volumetric flask and dissolved over 10 minutes by ultrasound in the solubilisation solvent, and then completed to volume.

The control and test solutions are filtered through a membrane (Sartorius membranes, 0.45 µm, ref: Minisart-RC-15).

Two test portions are taken per sample.

Calculation of Polyphenol Content

The polyphenol content is calculated using the following formula:

$$T_{polyphenol} = \frac{A_E \times m_T \times V_E}{A_T \times m_E \times V_T} \times d \times 100$$

T: content (as %) of polyphenol X of the extract
$A_E$: peak area of polyphenol X of the analyzed solution
$A_T$: peak area of polyphenol X of the standard solution
$m_E$: weight of the test portion of the analyzed solution (in mg)
$m_T$: weight of the test portion of the corresponding standard polyphenol X (in mg)
$V_T$: volume in which polyphenol X was solubilized (in mL)
$V_E$: volume in which the analyzed extract was solubilized (in mL)
d: dilution factor if necessary

EXAMPLES

I—Refined Raw Extracts:

I.1. Refined Extract No. 1

100 kg of fresh spinach leaves are extracted by macerating in 300 L of water at 50° C. for 2 hours.

Enzymes can be added to the water, of cellulose and hemi-cellulase type, or any other enzyme liquefying fruit or vegetables.

The loaded solvent (water) is separated from the solid matter in suspension and filtered.

Olive oil is added to the filtered, loaded solvent to the proportion of 1 kg of oil per kg of dry matter in the liquid.

The mixture of loaded solvent and oil is then concentrated by evaporation in vacuo in a falling film evaporator.

The heating temperature is maintained at a temperature below 60° C.

The concentrating operation is conducted until a 20-fold reduction of the total volume.

The concentrated mixture of oil/aqueous phase is then washed with soft water, at 10° C., to the proportion of 1 volume of water per volume of initial mixture.

This liquid-liquid extraction phase using a food oil, conducted during a concentration operation, allows all lipophilic components, particularly pigments, to be removed from the residual aqueous phase whilst preserving the entirety of the polyphenol components of interest.

The oil phase is separated and filtered, and forms a lipid solution of chlorophyll and carotenoid pigments. This solution can be directly used in food colouring preparations.

The aqueous concentrate forms a refined liquid extract (refined extract No. 1) which can be converted to powder by removing the solvent, by vacuum drying for example.

I.2. Refined Extract No. 2

100 kg of fresh spinach leaves are extracted by macerating in 30% vol. ethanol at 50° C. for 2 hours.

The loaded solvent (ethanol) is separated from the solid matter in suspension and filtered.

Grape-seed oil is added to the filtered solvent, to the proportion of 1 L of oil per kg of dry matter. A food antioxidant, of natural vitamin E type, can be added to the mixture.

The mixture is then dealcoholized by distillation and concentration under a high vacuum.

The concentrate obtained is separated into two by collecting the oil phase containing the chlorophyll and carotenoid pigments. The aqueous phase is collected separately.

This liquid-liquid extraction phase using food oil conducted during a concentrating operation allows all the lipophilic components, the pigments in particular, to be removed from the residual aqueous phase, whilst preserving the entirety of the polyphenol components of interest.

The pigment-concentrated oil phase can be used directly after filtering as green food colouring. It can also be dried on a substrate composed of maltodextrins, caseins and soy lecithins to obtain a green-colouring powder that is water-dispersible.

The aqueous concentrate forms a refined liquid extract (refined extract No. 2) which can be converted to a raw powder extract by removing the solvent, for example by vacuum drying or spray drying.

I.3. Refined Extract No. 3

100 kg of fresh spinach leaves are extracted by macerating in 90% vol. ethanol at 50° C. for 2 hours. The operation is repeated three times and all the collected liquid fractions are combined.

The loaded solvent (ethanol) is separated from the solid matter in suspension and then filtered.

Grape-seed oil is added to the filtered solvent to the proportion of 1 L oil per kg of dry matter. A food antioxidant of natural Vitamin E type may be added to the mixture.

The mixture is next dealcoholized by distillation and concentration under a high vacuum.

The concentrate obtained is separated into two by collecting the oil phase containing the chlorophyll and carotenoid pigments. The aqueous phase is collected separately.

This liquid-liquid extraction phase using food oil conducted during a concentrating operation allows all the lipophilic components, the pigments in particular, to be removed from the residual aqueous phase, whilst preserving the entirety of the polyphenol components of interest.

The pigment-concentrated oil phase can be used directly after filtering as greed food colouring. It can also be dried on a substrate composed of maltodextrins, caseins, and soy lecithins to obtain a green colouring powder that is water-dispersible.

The aqueous concentrate forms a refined liquid extract (refined extract No. 2) which can be converted to a raw powder extract by removing the solvent, by vacuum drying or spray drying for example.

II—Purified Extracts:

II.1. Purified Extract No. 1

The refined extract No. 2 is subjected to a purification step by chromatography on resin of divinylstyrenebenzene type (XAD 16 by Rohm & Haas), allowing an adsorption/desorption process suitable for polyphenols.

The adsorbed compounds are desorbed of the resin by washing with 60% vol. hydro-alcoholic solution at 35° C.

The eluent thus obtained then forms the purified extract which can also be preserved in liquid or dry form.

The composition of this purified extract in given in FIG. 1.

This extract therefore comprises the following compounds:

ferulic acid (peak n°5); patuletin-3-glucosyl-(1-6)-apiosyl (1-2)-glucoside (peak n°2); patuletin-3-glucosyl-(1-6)-glucoside (peak n°3); spinacetin-3-glucosyl-(1-6)-apiosyl(1-2)-glucoside (peak n°4); spinacetin-3-glucosyl-(1-6)-glucoside (peak n°5); spinacetin-3-feruloylglucosyl-(1-6)-glucoside (peak n°6); spinatoside (peak n°8); jaceidin-4'-glucuronide (peak n°9); 5,3',4'-trihydroxy-3-methoxy-6:7-methylenedioxyflavone-4'-glucuronide (peak n°10) and 5,4'-dihydroxy-3,3'-dimethoxy-6:7-methylenedioxyflavone-4'-glucuronide (peak n°11).

II.2. Purified Extract No. 2

The refined extract No. 3 is subjected to a purification step by liquid-liquid extraction using ethyl acetate.

The collected ethyl acetate contains the polyphenol fraction of interest, which then forms the purified extract which can also be preserved in liquid or dry form.

What is claimed is:

1. A method for preparing a concentrated spinach extract, in liquid or dry form, comprising a polyphenol titre equal to or greater than 50%, comprising purifying a raw spinach extract in liquid form by a liquid-liquid extraction technique with a food oil, wherein the food oil is selected from the group consisting of olive oil, sunflower oil, grape-seed oil, fish oil and mixtures thereof.

2. The method according to claim 1, characterized in that it comprises the following steps:
   adding the food oil to the raw spinach extract in liquid form, to obtain a raw liquid extract with added food oil,
   concentrating said raw liquid extract with added food oil by a vacuum concentration step under agitation, to obtain an aqueous phase comprising a water-soluble compound, and
   separating an oil phase and the aqueous phase.

3. The method according to claim 2, further comprising:
   collecting the oil phase,
   washing the oil phase with water one or more times, and
   optionally drying the oil phase to obtain a colouring powder from the spinach extract.

4. The method according to claim 2, further comprising collecting the aqueous phase then subjecting the aqueous phase to a purification step to obtain a purified concentrated extract.

5. The method according to claim 4, wherein the purification step is conducted by passing the aqueous phase through a chromatographic resin, wherein the resin is an ion exchange resin or an adsorption/desorption resin; or by a liquid-liquid extraction procedure using a solvent non-miscible in water, wherein the solvent is selected from the group consisting of ethyl acetate and butanol.

6. A method for preparing a colouring product from spinach, comprising the following steps:
   adding a food oil to a raw spinach extract in liquid form, wherein the food oil is selected from the group consisting of olive oil, sunflower oil, grape-seed oil, fish oil and mixtures thereof, to obtain a raw liquid extract with added food oil,
   concentrating said raw liquid extract with added food oil by a vacuum concentration step under agitation, to obtain an aqueous phase comprising a water-soluble compound,
   collecting an oil phase and washing the oil phase with water in one or more washing steps to obtain a liquid colouring product and, optionally,
   drying the washed oil phase to obtain a colouring powder.

7. A colouring product from spinach in liquid or dry form which is obtained according to claim 6.

* * * * *